US007341847B2

(12) United States Patent
Wang et al.

(10) Patent No.: US 7,341,847 B2
(45) Date of Patent: Mar. 11, 2008

(54) PROMOTER CONSTRUCT FOR GENE EXPRESSION IN NEURONAL CELLS

(75) Inventors: Shu Wang, Singapore (SG); Beihui Liu, Singapore (SG); Xu Wang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 597 days.

(21) Appl. No.: 10/407,009

(22) Filed: Apr. 2, 2003

(65) Prior Publication Data

US 2004/0197313 A1 Oct. 7, 2004

(51) Int. Cl.
*C12P 12/00* (2006.01)
*C07H 21/04* (2006.01)
*C12N 15/00* (2006.01)
*C12N 5/00* (2006.01)

(52) U.S. Cl. .................... 435/69.1; 536/23.1; 536/24.1; 435/320.1; 435/325

(58) Field of Classification Search ...................... None
See application file for complete search history.

(56) References Cited

U.S. PATENT DOCUMENTS

| | | | |
|---|---|---|---|
| 5,168,062 A | 12/1992 | Stinski | 435/240.2 |
| 5,310,660 A | 5/1994 | Bitter | 435/69.1 |
| 5,424,411 A | 6/1995 | Yagi et al. | 536/24.1 |
| 5,559,027 A | 9/1996 | Filmus et al. | 435/240.2 |
| 5,763,217 A * | 6/1998 | Cynader et al. | 435/69.1 |
| 5,811,633 A | 9/1998 | Wadsworth et al. | 800/2 |
| 5,849,522 A | 12/1998 | Fleckenstein et al. | 435/69.1 |
| 5,859,331 A | 1/1999 | Maas et al. | 800/205 |
| 5,877,399 A | 3/1999 | Hsiao et al. | 800/2 |
| 5,981,274 A | 11/1999 | Tyrrell et al. | 435/320.1 |
| 6,066,726 A | 5/2000 | Farb et al. | 536/24.1 |
| 6,180,855 B1 | 1/2001 | Kaplitt et al. | 514/44 |
| 6,218,140 B1 | 4/2001 | Fleckenstein et al. | 435/69.1 |
| 6,261,834 B1 | 7/2001 | Srivastava | 435/320.1 |
| 6,320,038 B1 | 11/2001 | Panula et al. | 536/24.1 |
| 2002/0090719 A1 | 7/2002 | Yew | 435/320.1 |

OTHER PUBLICATIONS

Hardy et al., Review, Science, 1998, 282: 1075-1079.*
Fisher et al., Review, Cell Mol Biol, 2001, 47: 1269-1275.*
Gardlik et al., Review, Med Sci Monit, 2005, 11: RA110-121.*
Tuszynski, Review, gene Therapy, 2003, 3: 815-828.*
Zhang et al., Molecular Brain Research, 2000, 84: 17-31.*
Xu et al., Hum Gene Ther, 2001, 12: 563-573.*
Peel et al., Gene Therapy, 1997, 4: 16-24.*
Huang et al., Hum Gene Therapy, 2001, 12: 1731-1740.*
Barnhart et al., Hum Gene Therapy, 1998, 9: 2545-2553.*
Bromberg et al., Methods in Enzymology, 2002, 346: 199-224.*
Submilla et al., Am J Physiol, 1999, 277: H2381-2391.*
Muller et al., FASEB J, 2000, 14: 2540-2548.*
Latham et al., Cancer Research, 2000, 60: 334-341.*
Meyer et al., Review, Cell. Mol. Biol., 2001, 47: 1277-1294.*
Lowenstein et al., Review, Current Opinion in Pharmacology, 2004, 4: 91-97.*
Fukuchi, K., et al. Activity Assays of Nine Heterogeneous Promoters In Neural and Other Cultured Cells. *In Vitro Cellular & Development Biology* (1994) 30A(5):300-5.
Thiel, G. et al. Characterization of Tissue-specific Transcription by the Human Synapsin I Gene Promoter. *Proceedings of the National Academy of Science* (1991) 88:3431-35. (See particularly Abstract and p. 3433, left hand column, line 26-47).
Haberman, R. P. et al. Differential neuronal gene expression from two non-specific promoters after recombinant adeno-associated virus (rAAV) 2 transduction in vivo. *Society for Neuroscience Abstracts*, (2001), vol. 27, No. 2, pp. 2345.
Zhang, G. et al. A tyrosine hydroxylase-neurofilament chimeric promoter enhances long-term expression in rat forebrain neurons from helper virus-free HSV-1 vectors. (2000) *Molecular Brian Research* 84:17-31. (see p. 18, right hand column, line 12-23, and Figure 1.
Gerdes C.A. et al. "Strong Promoters Are the Key to Highly Efficient, Noninflammatory and Noncytotoxic Adenoviral-Mediated Transgene Delivery into the Brain in Vivo". *Molecular Therapy*, vol. 2, No. 4, Oct. 2000, 330-338.
Khachigian, L, M. et al. Novel cis-Acting Elements in the Human Platelet-derived Growth Factor B-chain Core Promoter That Mediate Gene Expression in Cultured Vascular Endothelial Cells. *The Journal of Biological Chemistry*, 1994, vol. 269, No. 36, 22647-22656.
Klein R. L. et al. Neuron-Specific Transduction in the Rat Septohippocampal or Nigrostriatal Pathway by Recombinant Adeno-associated Virus Vectors. *Experimental Neurology*, 1998, 150:183-94.
Miller N. et al. "Targeted vectors for gene therapy". *FASEB J* 1995, 9: 190-199.
Miller N. et al. "Progress in Transcriptionally Targeted and Regulatable Vectors for Genetic Therapy". *Human Gene Therapy*, 1997, 8: 803-815.
Niwa, H. et al. "Efficient selection for high-expression transfectants with a novel eukaryotic vector:" *Gene* 1991, 108: 193-199.
Robinson, D. et al. "Retroviral vector with a CMV-IE/HIV-TAR hybrid LTR gives high basal expression levels and is up-regulated by HIV-1 Tat". *Gene Therapy*, 1995, 2: 269-278.
Sasahara, M. et al. "PDGF B-chain in Neurons of the Central Nervous System, Posterior Pituitary, and in a Transgenic Model". *Cell* 1991, 64: 217-227.
Sawicki, J.A. et al. "A Composite CMV-IE Enhancer/β-Actin Promoter is Ubiquitously Expressed in Mouse Cutaneous Epithelium". *Experimental Cell Research*, 1998, 244:367-369.

(Continued)

*Primary Examiner*—Joseph Woitach
*Assistant Examiner*—Ileana Popa
(74) *Attorney, Agent, or Firm*—Klarquist Sparkman LLP

(57) ABSTRACT

The invention relates to a chimeric promoter construct useful for neuronal cell specific gene expression. The invention provides a recombinant nucleic acid molecule that comprises a neuronal cell specific promoter such as platelet-derived growth factor β-chain promoter, operably linked to a heterologous enhancer which enhances the transcriptional activity of the promoter, such as cytomegalovirus immediate early gene enhancer. The promoter construct according to the invention can increase and prolong gene expression in neuronal cells and may be advantageously used in gene therapy of neuronal disorders.

25 Claims, 6 Drawing Sheets

OTHER PUBLICATIONS

Figure 1:
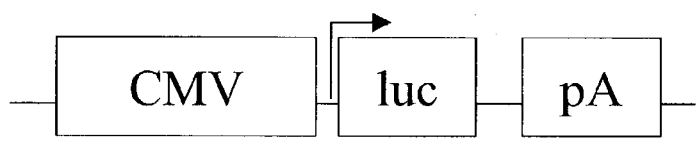
Figure 1:
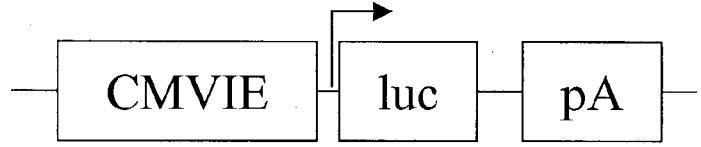
Figure 1:
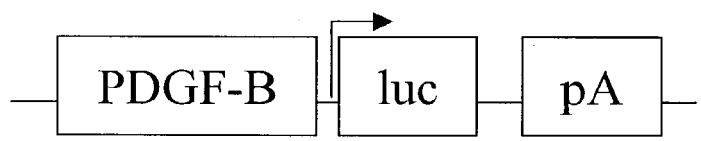
Figure 1:
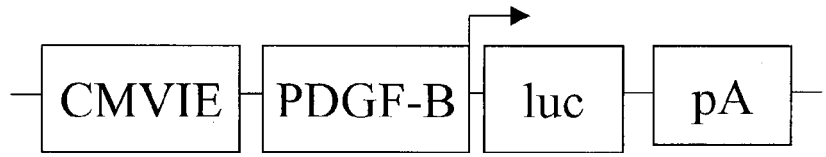

Yew, N. S. "Optimization of Plasmid Vectors for High-Level Expression in Lung Epithelial Cells". *Human Gene Therapy*, 1997, 8: 575-584.

Yew, N. S. "High and Sustained Transgene Expression in Vivo from Plasmid Vectors Containing a Hybrid Ubiquitin Promoter". *Molecular Therapy*, 2001, 4: 75-82.

Paterna, J.C., et al. "Influence of promoter and WHV post-transcriptional regulatory element on AAV-mediated transgene expression in the rat brain". *Gene Ther* Aug. 2000; 7(15): 1304-11.

Luebke, A.E., et al "Cochlear Function and Transgene Expression in the Guinea Pig Chochlea, Using Adenovirus- and Adeno-Associated Virus-Directed Gene Transfer". *Human Gene Therapy* 12:773-81 (May 1, 2001).

Mori, K., et al. "Intraocular Adenoviral Vector-Mediated Gene Transfer in Proliferative Retinopathies". *Investigative Opthalmology & Visual Science*, May 2002, vol. 43, No. 5, 1610-1615.

Hagstrom, J. N. et al. "Improved muscle-derived expression of human coagulation factor IX from a skeletal actin/CMV hybrid enhancer/promoter". *Blood*, Apr. 15, 2000, vol. 95, No. 8, 2536-2542.

Barnhart, K.M. et al Enhancer and Promoter Chimeras in Plasmids Designed for Intramuscular Injection: A Comparative In Vivo and In Vitro Study. *Human Gene Therapy* 9:2545-2553 (Nov. 20, 1998).

Factor P. "Gene Therapy for Acute Diseases" *Molecular Therapy*, vol. 4, No. 5, Dec. 2001, 515-524.

* cited by examiner pCMVluc pCMVIEluc pPDGFluc pCMVIE-PDGF-luc

NeuN　　　　　Luciferase　　　　Luciferase
　　　　　　　　　　　　　　　　　+
　　　　　　　　　　　　　　　　NeuN

A

B

PROMOTER CONSTRUCT FOR GENE EXPRESSION IN NEURONAL CELLS

FIELD OF THE INVENTION

The invention relates to a promoter construct useful for cell specific gene expression, more particularly expression in neuronal cells.

BACKGROUND OF THE INVENTION

Neurological illnesses such as stroke, epilepsy, head and spinal cord trauma, Parkinson's disease, Huntington's disease, Alzheimer's disease, amyotrophic lateral sclerosis, and many neurogenetic disorders have devastating effects on the individual and result in high social costs associated with chronic care and lost productivity. A common feature of these illnesses is neuronal loss. Many of the aforementioned disorders are related to the absence, malfunction or ineffectiveness of one gene or more and do not respond well to conventional therapeutic means. Gene transfer into the central nervous system (CNS), which involves the delivery and expression of a therapeutic gene, has, therefore, been considered as a potential approach to treatment of these disorders. This approach may mediate expression levels of neurotrophic factors, anti-apoptotic proteins, antioxidant molecules and other therapeutic factors to restore, halt or prevent neuronal degeneration. Gene therapy also offers much hope for the treatment of CNS malignancies.

The unique characteristics of the CNS, the most sophisticated organ in the body, presents several obstacles to successful gene therapy within the CNS. These characteristics include limited access to the CNS due to the physical barriers of the skull and the blood-brain barrier; the nature of terminally differentiated neurons and the difficulty of efficiently transfecting them with therapeutic genes. Moreover, the cell types found within the CNS are very diverse, many of which are critical to physiological functions and highly sensitive to any kinds of changes. This requires the development of CNS gene therapy that is restricted to a particular type of CNS cell, thus ensuring therapeutic effects in the desired cells and limiting side effects caused by gene expression in non-target CNS cells.

Specific gene expression in a selected cell type can be achieved at the level of targeted gene delivery through the use of ligand-associated delivery vectors that bind, via the ligands, to cell surface receptors that are unique to the target cells. Specific gene expression can also be achieved at the level of targeted transcription through the use of cell-specific promoters and enhancers. Cell-specific promoters are one of the primary means through which specialized cellular functions are limited to a particular differentiated cell type. The ability of these promoters to direct transcription of associated genes is regulated by the intracellular concentrations and activities of transcription factors in a specific type of cell.

Introduction of a transgene into a particular cell can sometimes result in disruption of or interference with cellular functions due to an excess of the transgene product. Due to their specificity, cell-specific promoters may give a level of transcription of a transgene that is acceptable to cellular metabolism, thus avoiding the exhaustion of protein synthesis materials and the over-accumulation of transgene products that may be toxic to transfected cells. Cell-specific promoters, because they are derived from genomic sequences, may also reduce the chance of activating host cell defense machinery and usually are less sensitive to cytokine-induced promoter inactivation than viral promoters. By using a cell-specific promoter, the stability of gene expression is expected to improve. However, the transcriptional activity of cell-specific cellular promoters is often weak, presenting a significant limitation on their use in gene therapy.

SUMMARY OF THE INVENTION

The present invention in one aspect provides a recombinant nucleic acid molecule comprising a neuronal cell specific PDGF β promoter operably coupled to a viral enhancer wherein the enhancer increases the neuronal cell specific transcriptional activity of the PDGF β promoter. In some embodiments, the promoter is platelet-derived growth factor β-chain promoter and the enhancer is cytomegalovirus immediate early gene enhancer element. In various embodiments, the recombinant nucleic acid molecule may further comprise operably linked therapeutic gene coding sequence.

The invention further provides an expression vector, a transgenic cell and non-human animals comprising a recombinant nucleic acid according to the invention. A method of expressing a gene in a neuronal cell comprising transforming a neuronal cell with such an expression vector is also provided.

The invention also provides a method of treating a neuronal disorder in a subject comprising administering to the subject an expression vector comprising a recombinant nucleic acid molecule described above operably linked to a therapeutic gene coding sequence.

In another aspect, the invention provides a method of increasing the cell-specific transcriptional activity of a neuronal cell specific PDGF β promoter comprising operably linking a heterologus viral enhancer to the PDGF β promoter.

FIGURES

FIG. 1. Schematic diagram of the promoter constructs tested in the PGL3 vector: full-length cytomegalovirus promoter (CMV); CMV immediate early gene enhancer (CMVIE); and platelet-derived growth factor β-chain promoter (PDGF β); and CMVIE-PDGF β. The position of the luciferase gene (luc) and the poly A tail (polyA) are also depicted.

Figure 2:
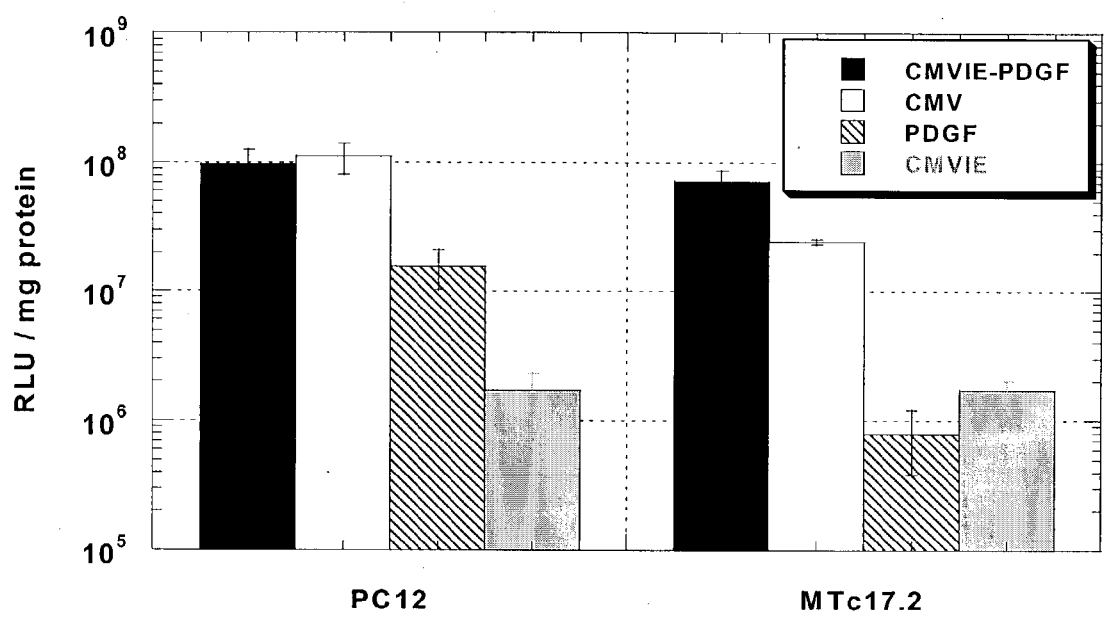

FIG. 2. Graphical representation of the luciferase activity levels for each of the promoter constructs, CMV, CMVIE, PDGF-β and CMVIE-PDGF β driving luciferase expression in neuronal PC12 and MTc17.2 cells after transient transfection. Luciferase activity was expressed in RLU per milligram of protein.

Figure 3:
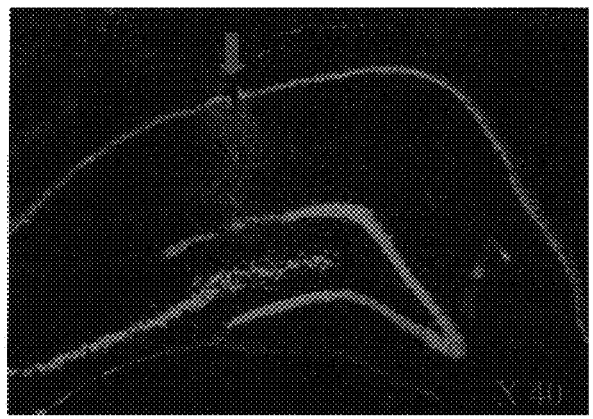
Figure 3:
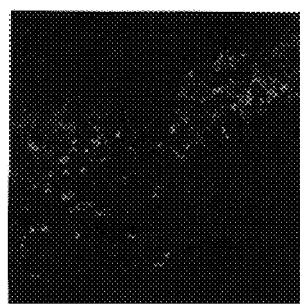
Figure 3:
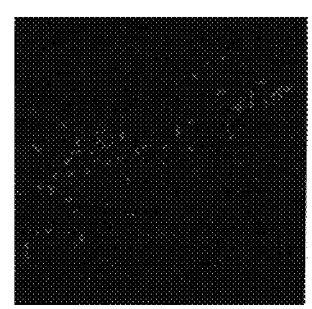
Figure 3:
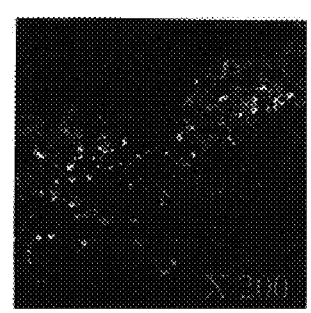

FIG. 3. Photomicrographs of immunohistochemical staining of the rat hippocampus 2 days post-injection of pCMVIE-PDGF β-luc. The hippocampus sections were stained with antibodies against luciferase protein and the NeuN marker.

Figure 4:
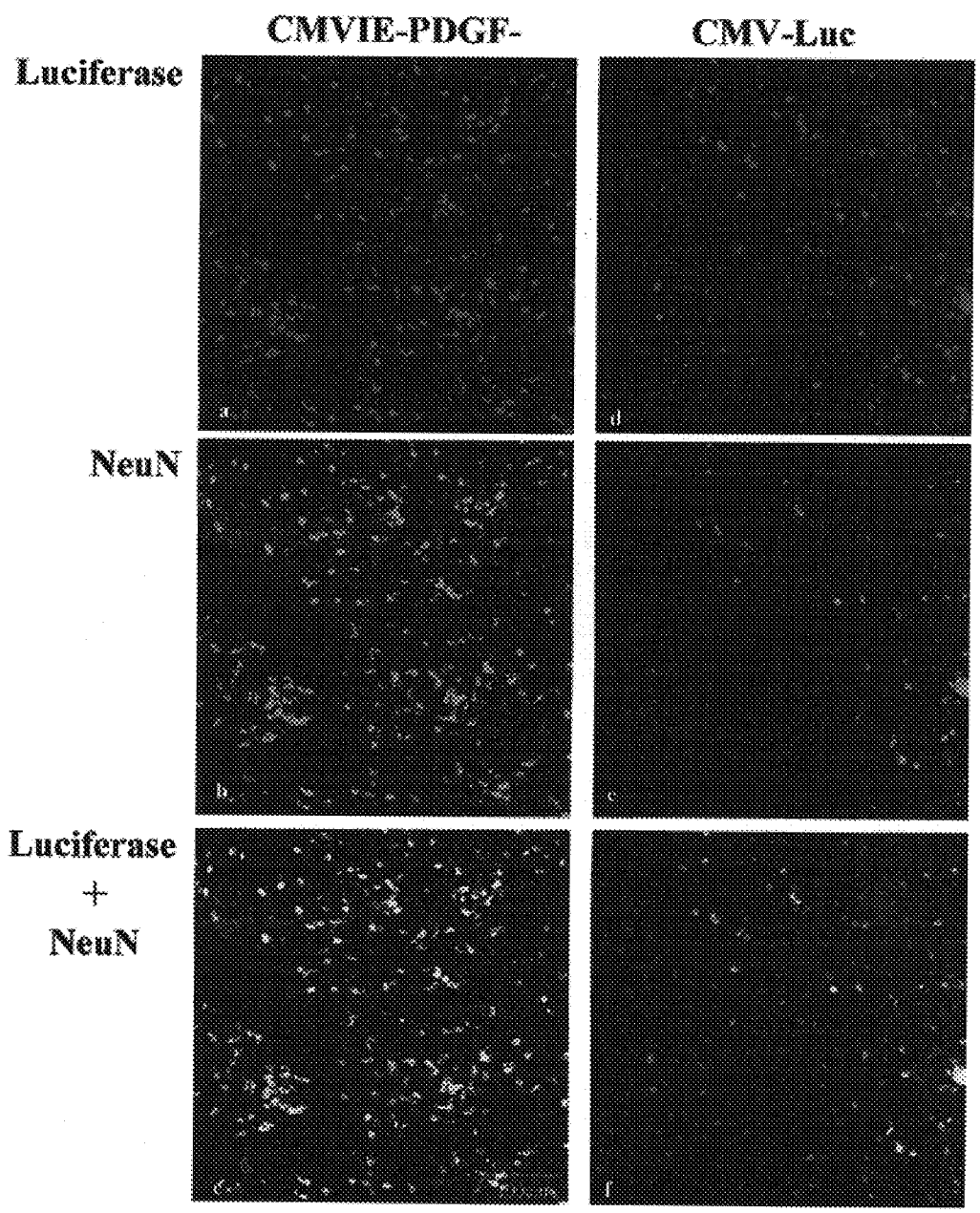

FIG. 4. High magnification photomicrographs showing double labeling of luciferase with NeuN in the rat striatum at 2 days post-injection of pCMVIE-PDGF β-luc (a, b, c) and pCMVluc (d, e, f).

Figure 5:
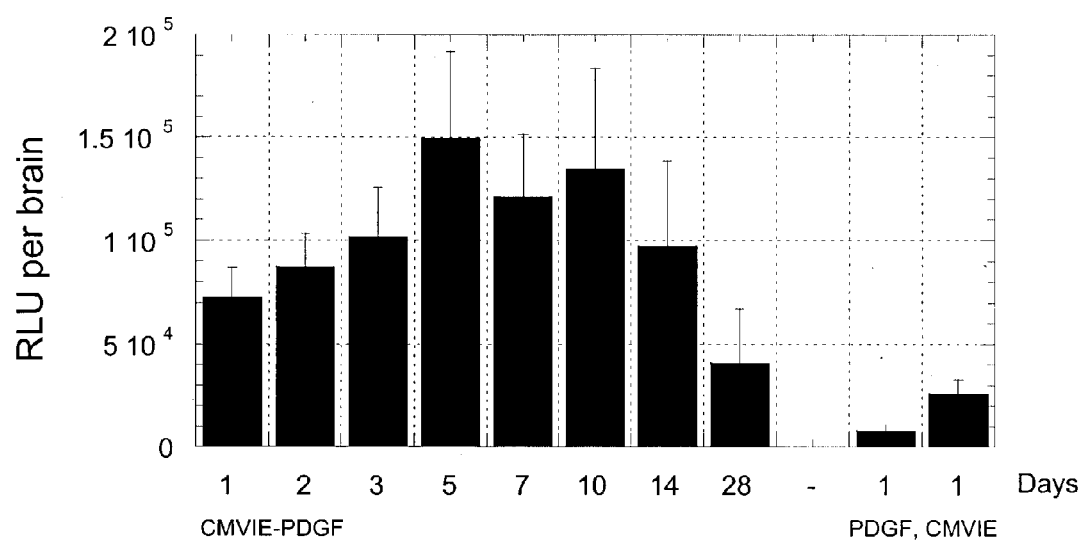

FIG. 5. Graphical representation of a time course assay of the average luciferase expression for each plasmid after stereotaxical injection into rat striatum. Values are presented as means+SEM.

Figure 6:
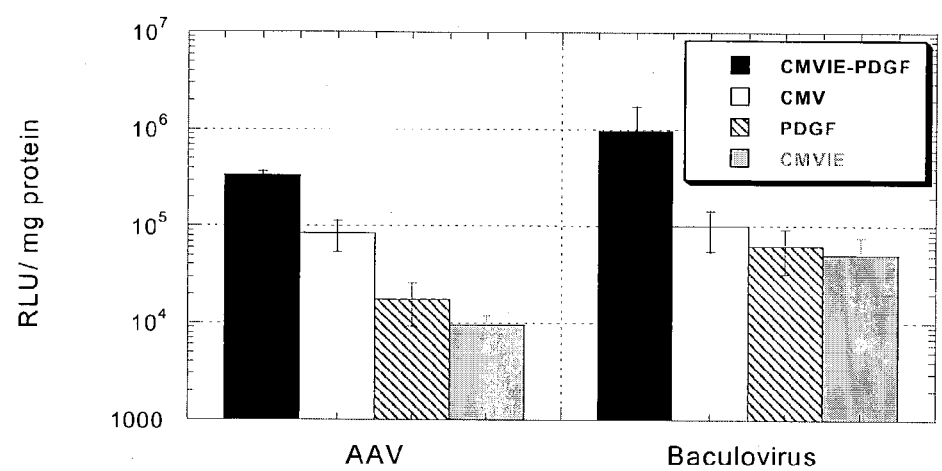
Figure 6:
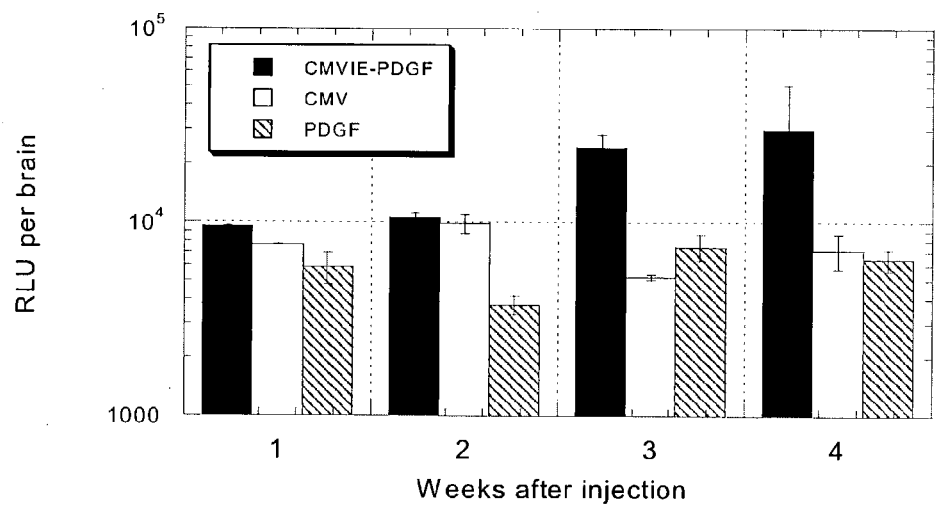

FIG. 6. A: Graphical representation of the luciferase activity levels for each of the promoter constructs, CMV, CMVIE, PDGF-β and CMVIE-PDGF driving luciferase expression in rat primary cortex neurons following adeno-associated virus (AAV) and baculovirus mediated transfection. Luciferase activity was expressed in RLU per milligram of protein. B: Graphical representation of a time course assay of the average luciferase expression for each promoter after stereotaxical injection of AAV vectors containing the promoter constructs into rat striatum. Values are presented as means+SEM.

DETAILED DESCRIPTION OF THE INVENTION

In various aspects, the present invention relates to gene expression and regulation of gene expression. The term "gene" is used in accordance with its usual definition, to mean an operably linked group of nucleic acid sequences.

The present invention provides a recombinant nucleic acid molecule comprising a chimeric transcription regulatory region that can activate transcription of sequences in neuronal cells when such sequences are operably linked to the regulatory region ("operably linked sequences"). The recombinant nucleic acid molecule of the invention comprises a neuronal cell specific promoter operably linked to a heterologous enhancer wherein the enhancer increases the neuronal cell specific transcriptional activity of the promoter. The terms "neuronal cell" and "neuron", which are used interchangeably herein, in accordance with the usual meaning refer to any conducting cell of the nervous system which typically includes the cell body, several dendrites and the axon. The term "recombinant" means that something has been recombined, such that reference to a recombinant nucleic acid molecule refers to a molecule that is comprised of nucleic acid sequences that are joined together or produced by means of molecular biological techniques.

The heterologous enhancer may be any nucleotide sequence which is not naturally operably linked to a neuronal cell specific promoter and which, when so operably linked, increases the neuronal cell specific transcriptional activity of the neuronal cell specific promoter. Reference to increasing the transcriptional activity is meant to refer to any detectable increase in the level of transcription of operably linked sequences compared to the level of the transcription observed with a neuronal cell specific promoter alone, as may be detected in standard transcriptional assays, including using a reporter gene construct as described in the Examples.

The enhancer therefore comprises at least one nucleotide sequence capable of increasing the neuronal cell specific transcriptional activity of the operably linked promoter. Generally, enhancers and promoters act to increase and/or activate transcription once bound by appropriate molecules such as transcription factors and the invention therefore encompasses embodiments in which such molecules are provided, either in vitro or in vivo. For example, and not to limit the invention, eukaryotic transcription factors include, but are not limited to NFAT, AP1, AP-2, Sp1, OCT-I, OCT-2, OAP, NF-KB, CREB, CTF, TFIIA, TFIIB, Pit-I, C/EBP, SRF (Mitchell P J and Tijan R (1989) Science 245:371; Eukaryotic transcription factor-DNA complexes. Patikoglou G, Burley S K. Annu Rev Biophys Biomol Struct 1997; 26:289-325.). In some embodiments, the nucleotide sequence effective to increase the transcriptional activity will retain the minimum binding site(s) for transcription factor(s) required for the sequence to act as an enhancer. As may be necessary to increase transcription of operably linked sequences to the desired extent, in some embodiments, the recombinant nucleic acid may comprise multiple copies of the same sequence or two or more different nucleotide sequence each of which is effective to increase the transcription. For various enhancers which may be used, transcription factor binding sites may be known or identified by one of ordinary skill using methods known in the art, for example by DNA footprinting, gel mobility shift assays, and the like. The factors may also be predicted on the basis of known consensus sequence motifs.

The enhancer may be a known strong viral enhancer or promoter element such as Rous sarcoma virus (RSV) promoter (Gorman C M, Merlino G T, Willingham M C, Pastan I, Howard B H. The Rous sarcoma virus long terminal repeat is a strong promoter when introduced into a variety of eukaryotic cells by DNA-mediated transfection. Proc Natl Acad Sci USA 1982; 79:6777-6781), SV40 promoter (Ghosh P K, Lebowitz P, Frisque R J, Gluzman Y. Identification of a promoter component involved in positioning the 5' termini of simian virus 40 early mRNAs. Proc Natl Acad Sci USA 1981; 78:100-104), CMV enhancer or promoter including CMV immediate early (IE) gene enhancer (CM-VIE enhancer) (Boshart M, Weber F, Jahn G, Dorsch-Hasler K, Fleckenstein B, Schaffner W. A very strong enhancer is located upstream of an immediate early gene of human cytomegalovirus. Cell 1985; 41:521-530; Niwa H, Yamamura H, Miyazaki J. Efficient selection for high-expression transfectants with a novel eukaryotic vector. Gene 1991; 108: 193-200; see also U.S. Pat. Nos. 5,849,522 and 5,168, 062). In a specific embodiment, the enhancer is human CMVIE enhancer and in one embodiment comprises the following sequence representing nucleotides −573 to −187 from the TATA box of the human CMV immediate early gene:

```
  1 CCTGGGTCGA CATTGATTAT TGACTAGTTA TTAATAGTAA TCAATACGGG (SEQ ID NO. 9)

51 GTCATTAGTT CATAGCCCAT ATATGGAGTT CCGCGTTACA TAACTTACGG

101 TAAATGGCCC GCCTGGCTGA CCGCCCAACG ACCCCCGCCC ATTGACGTCA

151 ATAATGACGT ATGTTCCCAT AGTAACGCCA ATAGGGACTT TCCATTGACG

201 TCAATGGGTG GACTATTTAC GGTAAACTGC CCACTTGGCA GTACATCAAG

251 TGTATCATAT GCCAAGTACG CCCCCTATTG ACGTCAATGA CGGTAAATGG

301 CCCCCTGGCA TTATGCCCAG TACATGACCT TATGGGACTT TCTACTTGGC

351 AGTACATCTA CGTATTAGTC ATCGCTATTA CCATGGT
```

The enhancer may also be allelic variants and derivatives (such as deletions, insertions, inversion, substitutions or addition of sequences) of this nucleotide sequence and other known enhancer sequences provided such variants or derivatives increases neuronal cell-specific transcription of operably linked sequences.

In various embodiments, such variants and derivatives may be substantially homologous in that it hybridizes to the sequence of SEQ ID NO 9 or other enhancer sequences under moderately or stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH. Stringent hybridization may for example be in 5 times SSC and 50% formamide at 42 degrees Celcius and washing in a wash buffer consisting of 0.1.times SSC at 65 degrees Celcius. Washes for stringent hybridization may for example be of at least 15 minutes, 30 minutes, 45 minutes, 60 minutes, 75 minutes, 90 minutes, 105 minutes or 120 minutes.

The degree of homology between sequences may also be expressed as a percentage of identity when the sequences are optimally aligned, meaning the occurrence of exact matches between the sequences. Optimal alignment of sequences for comparisons of identity may be conducted using a variety of algorithms, such as the local homology algorithm of Smith and Waterman,1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). In various embodiments, the variants and derivatives may be greater than 50%, 80% to 100%, at least 80%, at least 90% or at least 95% identical as determined using such algorithms.

The neuronal cell specific promoter may be any nucleotide sequence which functions to activate neuronal cell specific transcription, meaning that the sequence activates transcription of operably linked sequences in a neuronal cell and substantially not in other cell types. A promoter does not substantially activate transcription if the levels of transcription of operably linked sequences in any of those cell types are sufficiently low so as not to affect the physiological functioning of the cell. Neuronal cell specific promoters may include promoters for neuronal genes such as Synapsin I, Neuron-specific enolase, Neurofilament-L and Neuropeptide Y and promoters specific for particular types of neuronal cells. For example, tyrosine hydroxylase gene promoter (4.8 kb 5' UTR) is specific for catecholaminergic and the CNS neurons, dopamine-b-hydroxylase gene promoter is specific for adrenergic and noradrenegic neurons and L7 Purkinje cell protein promoter is specific for retinal rod bipolar neurons. For these and other neuronal cell specific promoters including, D1A dopamine receptor gene promoter, human hypoxanthine phosphoribosyltransferase promoter, SCG10 promoter, Tα1 α-tubulin promoter, aldolase C promoter, beta-tubulin gene promoter, GnRH gene enhancer and promoter, glutamate decarboxylase 65 gene promoter, beta-galactoside alpha1,2-fucosyltransferase gene promoter, neuronal nicotinic acetylcholine receptor beta3 gene promoter, GABA(A) receptor delta subunit gene promoter, neuron-specific FE65 gene promoter, N-type calcium channel alpha1B subunit gene promoter and microtubule-associated protein 1B gene promoters, see Harrington C A, Lewis E J, Krzemien D, Chikaraishi D M. Identification and cell type specificity of the tyrosine hydroxylase gene promoter.Nucleic Acids Res 1987, 15:2363-2384; Coker G T 3rd, Vinnedge L, O'Malley K L; Characterization of rat and human tyrosine hydroxylase genes: functional expression of both promoters in neuronal and non-neuronal cell types. Biochem Biophys Res Commun 1988, 157:1341-1347; Banerjee S A, Hoppe P, Brilliant M, Chikaraishi D M. 5' flanking sequences of the rat tyrosine hydroxylase gene target accurate tissue-specific, developmental, and transsynaptic expression in transgenic mice. J Neurosci 1992, 12:4460-4467; Morita S, Kobayashi K, Mizuguchi T, Yamada K, Nagatsu I, Titani K, Fujita K, Hidaka H, Nagatsu T. The 5'-flanking region of the human dopamine beta-hydroxylase gene promotes neuron subtype-specific gene expression in the central nervous system of transgenic mice. Brain Res Mol Brain Res 1993; 17:239-244; Ishiguro H, Kim K T, Joh T H, Kim K S. Neuron-specific expression of the human dopamine beta-hydroxylase gene requires both the cAMP-response element and a silencer region. J Biol Chem 1993; 268:17987-17994; Hoyle G W, Mercer E H, Palmiter R D, Brinster R L. Cell-specific expression from the human dopamine beta-hydroxylase promoter in transgenic mice is controlled via a combination of positive and negative regulatory elements. J Neurosci 1994, 14:2455-2463; Severynse D M, Colapietro A M, Box T L, Caron M G. The human D1A dopamine receptor gene promoter directs expression of a reporter gene to the central nervous system in transgenic mice. Brain Res Mol Brain Res 1995, 30:336-346; Mouradian M M, Minowa M T, Minowa T. Promoter structure of the human gene coding for the D1A dopamine receptor. Adv Neurol 1993, 60:343-345; Stout J T, Chen H Y, Brennand J, Caskey C T, Brinster R L. Expression of human HPRT in the central nervous system of transgenic mice. Nature 1985; 317:250-252; Rincon-Limas D E, Geske R S, Xue J J, Hsu C Y, Overbeek P A, Patel P I. 5'-flanking sequences of the human HPRT gene direct neuronal expression in the brain of transgenic mice. J Neurosci Res 1994; 38:259-267; Schwartz M L, Bruce J, Shneidman P S, Schlaepfer W W. Deletion of 3'-untranslated region alters the level of mRNA expression of a neurofilament light subunit transgene. J Biol Chem 1995; 270:26364-9; Forss-Petter S, Danielson P E, Catsicas S, Battenberg E, Price J, Nerenberg M, Sutcliffe J G. Transgenic mice expressing beta-galactosidase in mature neurons under neuron-specific enolase promoter control. Neuron 1990; 5:187-197; Twyman R M, Jones E A. Sequences in the proximal 5' flanking region of the rat neuron-specific enolase (NSE) gene are sufficient for cell type-specific reporter gene expression. J Mol Neurosci 1997; 8:63-73; Andersen J K, Garber D A, Meaney C A, Breakefield X O. Gene transfer into mammalian central nervous system using herpes virus vectors: extended expression of bacterial lacZ in neurons using the neuron-specific enolase promoter. Hum Gene Ther 1992; 3:487-499; Wuenschell C W, Mori N, Anderson D J. Analysis of SCG10 gene expression in transgenic mice reveals that neural specificity is achieved through selective derepression. Neuron 1990; 4:595-602; Mori N, Stein R, Sigmund O, Anderson D J. A cell type-preferred silencer element that controls the neural-specific expression of the SCG10 gene. Neuron 1990; 4:583-594; Hoesche C, Sauerwald A, Veh R W, Krippl B, Kilimann M W. The 5'-flanking region of the rat synapsin I gene directs neuron-specific and developmentally regulated reporter gene expression in transgenic mice. J Biol Chem 1993; 268:26494-26502; Kilic E, Hermann D M, Kugler S, Kilic U, Holzmuller H, Schmeer C, Bahr M. Adenovirus-mediated Bcl-X(L) expression using a neuron-specific synapsin-1 promoter protects against disseminated neuronal injury and brain infarction following focal cerebral ischemia in mice. Neurobiol Dis 2002; 11:275-284; Gloster A, Wu W, Speelman A, Weiss S, Causing C, Pozniak C, Reynolds B, Chang E, Toma J G, Miller F D. The T alpha 1 alpha-tubulin promoter specifies gene expression as a function of neuronal growth and regeneration in transgenic mice. J Neurosci 1994; 14:7319-7330; Thomas M, Makeh I, Briand P, Kahn A, Skala H. Determinants of the brain-specific expression of the rat aldolase C gene: ex vivo and in vivo analysis. Eur J Biochem 1993; 218:143-151; Thomas M, Skala H, Kahn A, Tuy F P. Functional dissection of the brain-specific rat aldolase C gene promoter in transgenic mice. Essential role of two GC-rich boxes and an HNF3 binding site. J Biol Chem 1995; 270:20316-20321; Dennis K, Uittenbogaard M, Chiaramello A, Moody S A. Cloning and characterization of the 5'-flanking region of the rat neuron-specific Class III beta-tubulin gene. Gene 2002 294:269-277; Waldbieser G C, Minth C D, Chrisman C L, Dixon J E. Tissue-specific expression of the human neuropeptide Y gene in transgenic mice. Brain Res Mol Brain Res 1992; 14:87-93; Lawson M A, Macconell L A, Kim J, Powl B T, Nelson S B, Mellon P L. Neuron-specific expression in vivo by defined transcription regulatory elements of the GnRH gene. Endocrinology 2002; 143:1404-1412; Wolfe A, Kim H H, Tobet S, Stafford D E, Radovick S. Identification of a discrete promoter region of the human GnRH gene that is sufficient for directing neuron-specific expression: a role for POU homeodomain transcription factors. Mol Endocrinol 2002; 16:435-449; Makinae K, Kobayashi T, Kobayashi T, Shinkawa H, Sakagami H, Kondo H, Tashiro F, Miyazaki J, Obata K, Tamura S, Yanagawa Y. Structure of the mouse glutamate decarboxylase 65 gene and its promoter: preferential expression of its promoter in the GABAergic neurons of transgenic mice. J Neurochem 2000; 75:1429-14371; Hitoshi S, Kusunoki S, Kanazawa I, Tsuji S. Dorsal root ganglia neuron-specific promoter activity of the rabbit beta-galactoside alpha1,2-fucosyltransferase gene. J Biol Chem 1999; 274:389-396; Roztocil T, Matter-Sadzinski L, Gomez M, Ballivet M, Matter J M. Functional properties of the neuronal nicotinic acetylcholine receptor beta3 promoter in the developing central nervous system. J Biol Chem 1998; 273:15131-15137; Luscher B, Hauselmann R, Leitgeb S, Rulicke T, Fritschy J M. Neuronal subtype-specific expression directed by the GABA(A) receptor delta subunit gene promoter/upstream region in transgenic mice and in cultured cells. Brain Res Mol Brain Res 1997; 51:197-211; Zambrano N, De Renzis S, Minopoli G, Faraonio R, Donini V, Scaloni A, Cimino F, Russo T. DNA-binding protein Pur alpha and transcription factor YY1 function as transcription activators of the neuron-specific FE65 gene promoter. Biochem J 1997; 328:293-300; Kim D S, Jung H H, Park S H, Chin H. Isolation and characterization of the 5'-upstream region of the human N-type calcium channel alpha1B subunit gene. Chromosomal localization and promoter analysis. J Biol Chem 1997; 272:5098-5104 and Liu D, Fischer I. Two alternative promoters direct neuron-specific expression of the rat microtubule-associated protein 1B gene. J Neurosci 1996; 16:5026-5036. Other neuronal specific promoters will be known to persons skilled in the art and suitable promoter/enhancer constructs may be readily determined by standard expression assays, including as described in the Examples.

The promoter comprises at least one nucleotide sequence capable of activating neuronal cell specific expression of operably linked sequences and in some embodiments the nucleotide sequence will retain the minimum binding site(s) for transcription factor(s) required for the sequence to act as a promoter. In some embodiments, the recombinant nucleic acid comprises multiple copies of the same sequence or two or more different nucleotide sequences each of which is effective to activate the transcription activity. For various promoters which may be used, transcription factor binding sites may be known or identified by one of ordinary skill using methods known in the art as described above.

Platelet-derived growth factor β-chain (PDGF β) promoter (Sasahara M, Fries J W, Raines E W, Gown A M, Westrum L E, Frosch M P, Bonthron D T, Ross R, Collins T. PDGF β-chain in neurons of the central nervous system, posterior pituitary, and in a transgenic model. Cell 1991; 64:217-227) has been shown to be specific for CNS neuronal cells, including dopaminergic neurons and in one embodiment, the neuronal cell specific promoter is PDGF β promoter. In a specific embodiment, the neuronal specific promoter is human PDGF β promoter and in one embodiment the neuronal cell specific promoter comprises the following sequence representing nucleotides −1492 to −5 from the transcription start site of the human PDGF β gene:

```
  1 CTAGAGGATC CACAGTCTCC TGAGTAGCTG GGACTACAGG AGCTTGTTAC (SEQ ID NO. 10)

51 CACACCCAGC TCCAGTTTAT AAATTCATCT CCAGTTTATA AAGGAGGAAA

101 CCGAGGTACT GAGAGGTTAA AAAACCTTCC TGCAGACACT TGTCCAGCAA

151 GTGGCCACTC CAGGATTTGG ACCAAGGTGA TGTGTCTTCA GGCTGTGTCT

201 CTGCCACTGT GCCACGCTGC TGGGTGGTAG GCAGCAGTGG GTGGGTGCCT

251 GCAGTGGTCT GTAAAGACCA CCTGAGATGT CCTTCCTCCT CTGTTCCACC

301 CTGTCCAGGT CCAAGAAGAC AGTCTATGAA GAGAGAGCAG GTGTGACTCT
```

-continued

```
 351 CTCAGTGTGC TCCTCTGTGA GAAGCAGGCT GACATCCCAA AGGGAAGGGC

401 GGATAACAGA GACAGTGCAA GCGGAGGAGA TGAGGGTGCC TCAAAGCCGG

451 GAGGCTGGGT GATGCAGGAG CCTGCGTGTC CCGAGGGGGG TGCTGGGCCC

501 AGTGTGAGTA CGTGTGACTG TGACTGAGAC AGTGTGACTG CTGAAGGCAG

551 GGACACAGCA GCTCCCTGAC TGGGGGCAGA AGGCGTTAAC TGTGTGAAGG

601 CTGGTTGTGG GTGGGTGGGC TCTGGGCCTC GAACCCGGGG GCTGAGGGAG

651 ATAGTAAACA GCAGGGTGAC TGACGGGAAG ATCATGTTGG TAGCCCTGCG

701 AAGATGCTGC AGGGCTGTGG GGGTTTGTGT GACTTTGCAG TTCAACAAAT

751 TCAAATTCAG CCAACGCTGG CAGGGCCTGT TGTGCCAGGC AACCAGCTAG

801 GAGGAGGAGA CTCGGACCCA GCTTGCAGCT GAAGGGCGCT GGCTGCCGGG

851 TTCTGTGGGT TCACCTTGCG GTGTCTTCCC TTGCTAACAC TGAGTCCTTA

901 CAATAGCCCC ATCTCCAGGT TGAGGCTAGA TGGAGGGGAC AGAGGGAAGT

951 GACTTGCCCA AGGTGACCCA AGCTCCCGAG TGCCAGGGCA GGATCTGAAT

1001 TCAGGCTCTC AGACTGCAGA GCCTGAGTCC CTCCCTGCCA TGCCTGTGCC

1051 AGGGTGGAAA TGTCTGGTCC TGGAGGGGAG CGTGGACTCC TGGCCTTGGC

1101 TCTGGAGACA TCCCCCTAGA CCACGTGGGC TCCTAACCTG TCCATGGTCA

1151 CTGTGCTGAG GGGCGGGACG GTGGGTCACC CCTAGTTCTT TTTTCCCCAG

1201 GGCCAGATTC ATGGACTGAA GGGTTGCTCG GCTCTCAGAG ACCCCCTAAG

1251 CGCCCCGCCC TGGCCCCAAG CCCTCCCCCA GCTCCCGCGT CCCCCCCCTC

1301 CTGGCGCTGA CTCCGGGCCA GAAGAGGAAA GGCTGTCTCC ACCCACCTCT

1351 CGCACTCTCC CTTCTCCTTT ATAAAGGCCG GAACAGCTGA AAGGGTGGCA

1401 ACTTCTCCTC CTGCAGCCGG GAGCGGCCTG CCTGCCTCCC TGCGCACCCG

1451 CAGCCTCCCC CGCTGCCTCC CTAGAGTCGA GGAACTAA
```

The promoter may also comprise allelic variants and derivatives (such as deletions, insertions, inversion, substitutions or addition of sequences) of this nucleotide sequence and other neuronal cell specific promoter sequences provided such variants or derivatives activate neuronal cell-specific transcription of operably linked sequences. In various embodiments, such variants and derivatives may be substantially homologous as that term is used above, or greater than 50%, 80% to 100% at least 80%, at least 90% or at least 95% identical as determined using algorithms described above.

A first nucleic acid sequence is operably linked with a second nucleic acid sequence when the sequences are placed in a functional relationship. For example, a coding sequence is operably linked to a promoter if the promoter activates the transcription of the coding sequence. Similarly, a neuronal cell specific promoter and a heterologous enhancer are operably linked when the enhancer increases the neuronal cell specific transcription of operably linked sequences. Enhancers may function when separated from promoters and as such, an enhancer may be operably linked to a neuronal cell specific promoter but may not be contiguous. Generally, however, operably linked sequences are contiguous.

In an embodiment of the present invention, CMVIE enhancer is operably linked upstream to PDGF β promoter. In a further embodiment, CMVIE enhancer is operably linked upstream to PDGF β promoter and the two sequences are contiguous.

In an embodiment of the invention, the recombinant nucleic acid molecule comprises the following sequence consisting of SEQ ID NO. 9 upstream of SEQ ID NO. 10 and a linker sequence between SEQ ID NO. 9 and 10:

```
5' CCTGGGTCGACATTGATTATTGACTAGTTATTAATAGTAATCAATACGGGGTCATTAGTTCATAGCC   (SEQ ID NO. 11)

CATATATGGAGTTCCGCGTTACATAACTTACGGTAAATGGCCCGCCTGGCTGACCGCCCAACGACCCCC

GCCCATTGACGTCAATAATGACGTATGTTCCCATAGTAACGCCAATAGGGACTTTCCATTGACGTCAAT

GGGTGGACTATTTACGGTAAACTGCCCACTTGGCAGTACATCAAGTGTATCATATGCCAAGTACGCCCC

CTATTGACGTCAATGACGGTAAATGGCCCCCTGGCATTATGCCCAGTACATGACCTTATGGGACTTTCT
```

-continued

```
ACTTGGCAGTACATCTACGTATTAGTCATCGCTATTACCATGGTGAGCTCCTAGAGGATCCACAGTCTC

CTGAGTAGCTGGGACTACAGGAGCTTGTTACCACACCCAGCTCCAGTTTATAAATTCATCTCCAGTTTA

TAAAGGAGGAAACCGAGGTACTGAGAGGTTAAAAAACCTTCCTGCAGACACTTGTCCAGCAAGTGGCCA

CTCCAGGATTTGGACCAAGGTGATGTGTCTTCAGGCTGTGTCTCTGCCACTGTGCCACGCTGCTGGGTG

GTAGGCAGCAGTGGGTGGGTGCCTGCAGTGGTCTGTAAAGACCACCTGAGATGTCCTTCCTCCTCTGTT

CCACCCTGTCCAGGTCCAAGAAGACAGTCTATGAAGAGAGAGCAGGTGTGACTCTCTCAGTGTGCTCCT

CTGTGAGAAGCAGGCTGACATCCCAAAGGGAAGGGCGGATAACAGAGACAGTGCAAGCGGAGGAGATGA

GGGTGCCTCAAAGCCGGGAGGCTGGGTGATGCAGGAGCCTGCGTGTCCCGAGGGGGGTGCTGGGCCCAG

TGTGAGTACGTGTGACTGTGACTGAGACAGTGTGACTGCTGAAGGCAGGGACACAGCAGCTCCCTGACT

GGGGGCAGAAGGCGTTAACTGTGTGAAGGCTGGTTGTGGGTGGGTGGGCTCTGGGCCTCGAACCCGGGG

GCTGAGGGAGATAGTAAACAGCAGGGTGACTGACGGGAAGATCATGTTGGTAGCCCTGCGAAGATGCTG

CAGGGCTGTGGGGGTTTGTGTGACTTTGCAGTTCAACAAATTCAAATTCAGCCAACGCTGGCAGGGCCT

GTTGTGCCAGGCAACCAGCTAGGAGGAGGAGACTCGGACCCAGCTTGCAGCTGAAGGGCGCTGGCTGCC

GGGTTCTGTGGGTTCACCTTGCGGTGTCTTCCCTTGCTAACACTGAGTCCTTACAATAGCCCCATCTCC

AGGTTGAGGCTAGATGGAGGGGACAGAGGGAAGTGACTTGCCCAAGGTGACCCAAGCTCCCGAGTGCCA

GGGCAGGATCTGAATTCAGGCTCTCAGACTGCAGAGCCTGAGTCCCTCCCTGCCATGCCTGTGCCAGGG

TGGAAATGTCTGGTCCTGGAGGGGAGCGTGGACTCCTGGCCTTGGCTCTGGAGACATCCCCCTAGACCA

CGTGGGCTCCTAACCTGTCCATGGTCACTGTGCTGAGGGGCGGGACGGTGGGTCACCCCTAGTTCTTTT

TTCCCCAGGGCCAGATTCATGGACTGAAGGGTTGCTCGGCTCTCAGAGACCCCCTAAGCGCCCCGCCCT

GGCCCCAAGCCCTCCCCCAGCTCCCGCGTCCCCCCCCTCCTGGCGCTGACTCCGGGCCAGAAGAGGAAA

GGCTGTCTCCACCCACCTCTCGCACTCTCCCTTCTCCTTTATAAAGGCCGGAACAGCTGAAAGGGTGGC

AACTTCTCCTCCTGCAGCCGGGAGCGGCCTGCCTGCCTCCCTGCGCACCCGCAGCCTCCCCCGCTGCCT

CCCTAGAGTCGAGGAACTAA3'
```

The recombinant nucleic acid molecule may also comprise at least one operably linked coding sequence. In various embodiments, the operably linked sequence may a encode reporter protein such as luciferase or green fluorescence protein or may be a therapeutic gene sequence.

In some embodiments, to be operably linked, the neuronal cell specific promoter and the heterologous enhancer may be located on the same strand as the operably linked sequences and in some embodiments, 5' of the operably linked sequences. In such embodiments, the promoter may be directly 5' of the operably linked sequences or there may be intervening sequences between these regions. In some embodiments the promoter and enhancer may be located 3' of the operably linked sequences. In one embodiment, one or more coding sequences are linked downstream to PDGF β promoter. In a further embodiment, one or more coding sequences are linked downstream and contiguous to PDGF β promoter.

The recombinant nucleic acid molecule of the present invention may be constructed by standard techniques known to one skilled in the art and described, for example, in Sambrook et al. (2001) in Molecular Cloning: A Laboratory Manual, 3rd Edition, Cold Spring Harbor, Laboratory Press, and other laboratory manuals. In various aspects of the invention, nucleic acid molecules may be chemically synthesized using techniques such as are disclosed, for example, in Itakura et al. U.S. Pat. No. 4,598,049; Caruthers et al. U.S. Pat. No. 4,458,066; and Itakura U.S. Pat. Nos. 4,401,796 and 4,373,071. Such synthetic nucleic acids are by their nature "recombinant" as that term is used herein (being the product of successive steps of combining the constituent parts of the molecule).

In alternative embodiments, isolated nucleic acids may be combined. By isolated, it is meant that the isolated substance has been substantially separated or purified away from other components, such as biological components, with which it would otherwise be associated, for example in vivo, so that the isolated substance may itself be manipulated or processed. The term 'isolated' therefore includes substances purified by standard purification methods, as well as substances prepared by recombinant expression in a host, as well as chemically synthesized substances. A promoter is, for example, isolated when it is not immediately contiguous with (i.e., covalently linked to) the coding sequences with which it is normally contiguous in the naturally occurring genome of the organism from which it is derived. A variety of strategies are available for combing or ligating fragments of DNA, and depending on the nature of the termini of the DNA fragments, a suitable strategy will be readily apparent to persons skilled in the art.

Another aspect of the invention provides an expression vector comprising the recombinant nucleic acid molecule of the invention. The vector may be a plasmid or a virus or virus derived. The construction of such a vector by standard techniques will also be well known to one of ordinary skill in the art. The vectors of the present invention may also contain other sequence elements to facilitate vector propagation and selection in host cells for example, coding sequences for selectable markers, and reporter genes, known to persons skilled in the art. In addition, the vectors of the present invention may comprise a sequence of nucleotides for one or more restriction endonuclease recognition sites.

In one embodiment, a plasmid expression vector may be constructed by inserting CMVIE enhancer and PDGF β promoter into the multiple cloning site of the pGL3 plasmid (Promega) as described in the Examples. In the resulting vector, the promoter construct of the invention is operably linked to the luciferase reporter gene contained within the pGL3 plasmid. In some embodiments, a viral expression vector may be constructed by inserting CMVIE enhancer and PDGF β promoter into AAV and vaculovirus as described in the Examples An expression vector of the present invention may be introduced into a host cell, which may include a cell capable of expressing the protein encoded by the expression vector. The host cell may include both cultured neuronal cells, including neuronal cell lines, cultured neuronal stem cells and primary neurons, and a neuronal cell within a living organism. Accordingly, the invention also provides host cells containing an expression vector of the invention. The term "host cell" refers not only to the particular subject cell but to the progeny or potential progeny of such a cell. Because certain modifications may occur in succeeding generations due to either cellular differentiation, mutation or environmental influences, in fact, be identical to the parent cell, but are still included within the scope of the term as used herein.

Vector DNA can be introduced into cells by conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells are well known in the art and can for example be found in Sambrook et al. (Molecular Cloning: A Laboratory Manual, 3rd Edition, Cold Spring Harbor Laboratory press (2001)), and other laboratory manuals.

A cell, tissue, organ, or organism into which has been introduced a foreign nucleic acid, is considered "transformed", "transfected", or "transgenic". A transgenic or transformed cell or organism also includes progeny of the cell or organism and progeny produced from a breeding program employing a transgenic organism as a parent and exhibiting an altered phenotype resulting from the presence of a recombinant nucleic acid construct. A transgenic organism is therefore an organism that has been transformed with a heterologous nucleic acid, or the progeny of such an organism that includes the transgene.

The invention in various aspects provides a transgenic cell and a non-human animal comprising a recombinant nucleic acid molecule according to various embodiments of the invention.

For stable transfection of mammalian cells, it is known that, depending upon the expression vector and transfection technique used, only a small fraction of cells may integrate the foreign DNA into their genome. In order to identify and select these integrants, a gene that encodes a selectable marker (such as resistance to antibiotics) may be introduced into the host cells along with the gene of interest. Preferred selectable markers include those that confer resistance to drugs, such as G418, hygromycin and methotrexate. Nucleic acids encoding a selectable marker may be introduced into a host cell on the same vector as that encoding the peptide compound or may be introduced on a separate vector. Cells stably transfected with the introduced nucleic acid may be identified by drug selection.

As further described in the examples below, an embodiment of the invention, which combines CMVIE enhancer with PDGF β promoter, can increase the level of transcription while maintaining neuronal cell specificity, both in vivo and in vitro.

PDGF β is heavily expressed in neurons of the central nervous system and a PDGF β promoter fragment has been characterized to target the expression of transgenes to differentiated neurons in transgenic animals. However, PDGF β promoter is relatively a poor activator of transcription even compared with other neuron-specific promoters.

By combining CMVIE enhancer with PDGF-β promoter, the inventors have been able to achieve for the first time a promoter construct which is specific for neuronal cells and which can activate transcription of operably linked sequences at a higher level and for a longer period than with PDGF β promoter alone. A recombinant adeno-associated virus vector containing PDGF β promoter has previously been demonstrated to be able to transduce significantly more dopaminergic neurons than titer-matched vectors carrying CMV promoter. It was therefore surprising that CMVIE enhancer when combined with PDGF β promoter can increase the level of transcriptional activity in neuronal cells.

The result was also surprising given that CMV promoter has been shown to be variable in its activities in different cells of the nervous system. A transgene driven by CMV promoter tends to be expressed in the ventricular zone, radial fibers and migrating neuroblasts in the developing brain, but not in mature neurons. This observation is consistent with the finding that CMV infection accounts for little debilitation in adult humans but can be disastrous in the developing human brain, partly due to higher levels of expression of CMV promoter in developing neurons. Transgenic studies in adult brains of mice have shown restricted expression from CMV promoter in limited types of neurons. A recent paper has reported astrocyte-specific expression when the murine CMV promoter was used. Similarly, baculovirus vectors containing CMV promoter mediated expression primarily in glial cells in adult brains, whereas neuronal expression was observed when the Rous sarcoma virus long terminal repeat (RSV LTR) promoter was used. The variance of these reports is likely related to the observation that slight changes in the CMV promoter sequence generate completely different patterns of expression in CNS neurons. This sequence-specific expression is due in part to the complexity of the CMV promoter that contains binding sites for cAMP, CREB/ATF, NF-κB, SP1, YY1, retinoic acid, AP-1, NF1, its own immediate early protein product, as well containing a methylation signal sequence.

It appears, however, when combined with a neuronal cell specific promoter such as PDGF-β promoter, CMVIE enhancer can increase and prolong neuronal cell specific transcription of operably linked sequences. The present invention therefore addresses a major limitation of using a neuronal cell specific promoter in gene therapy.

While CMVIE enhancer and PDGF β promoter construct described below illustrates an embodiment of the invention, it will be apparent to those skilled in the art that other constructs may be readily identified by standard expression assays. Each of PDGF β promoter and CMVIE enhancer when combined with a suitable enhancer or promoter as the case may be can provide a promoter construct that may be suitable for gene expression in neuronal cells. Other suitable neuronal promoters therefore may be identified by combining a promoter which can activate a neuronal cell specific expression with CMVIE enhancer and determining the increase in the expression of operably linked sequences enhancer in neuronal cells. Similarly, other suitable enhancers may be identified by combining a heterologous enhancer with PDGF-β promoter and determining an increase in the expression of operably linked sequences in neuronal cells. Such other suitable enhancers and promoters may be combined to form other exemplary embodiments of the invention.

The invention in one aspect provides a method of enhancing the transcriptional activity of a neuronal cell specific promoter comprising operably linking a heterologous enhancer to the neuronal cell specific promoter. In various embodiments, the enhancer and the promoter may be as described above, including human CMVIE enhancer and human PDGF β promoter. In an embodiment, the enhancer is operably linked upstream to the neuronal cell specific promoter.

The recombinant nucleic acid molecule, in its various embodiments may be used to express exogenous DNA sequences in neuronal cells, for example to study gene function and regulation of gene expression in neuronal cells.

High level, long term and cell specific gene expression are required to effectively treat many neurological disorders by gene therapy. The recombinant nucleic acid molecule, in one embodiment, may therefore be advantageously used in gene therapy to treat neuronal disorders, including stroke, ischemia, epilepsy, head and spinal cord trauma, Parkinson's diseases, Huntington's disease, Alzheimer's disease, amyotrophic lateral sclerosis, and neurogenetic disorders. For example, in Parkinson's disease, a progressive loss of dopaminergic neurons in the substantia nigra ultimately results in a dopamine deficiency and associated motor impairments. An expression vector comprising the CMVIE enhancer and PDGF β promoter construct therefore should be useful for developing gene therapy for Parkinson's disease that rely on optimal vectors to transfer therapeutic genes into dopaminergic neurons.

The invention in one aspect provides a method of treating a neuronal disorder in a subject comprising administering to the subject an expression vector comprising the recombinant nucleic acid of the invention operably linked to a therapeutic gene sequence. Therapeutic genes include growth factor genes (which include genes of fibroblast growth factor gene family, nerve growth factor gene family and insulin-like growth factor genes), and antiapoptotic genes (including genes of bcl-2 gene family).

Methods for introducing DNA into mammalian cells in vivo are known, including for gene therapy and may be used to administer the expression vector DNA of the invention to a subject for gene therapy of neurological disorders. A nucleic acid of the invention may be delivered to cells in vivo using methods such as direct injection of DNA, receptor-mediated DNA uptake, viral-mediated transfection or non-viral transfection and lipid based transfection, all of which may involve the use of gene therapy vectors. A delivery apparatus (e.g., a "gene gun") for injecting DNA into cells in vivo may be used. Such an apparatus may be commercially available (e.g., from BioRad). In one embodiment, the expression vector is administered by direct injection into the central nervous system or to the cerebrospinal fluid.

Retrovirus-mediated gene delivery for use as gene therapy has been well characterized and protocols for producing recombinant retroviruses and for infecting cells in vitro or in vivo with such viruses can be found in Current Protocols in Molecular Biology, Ausubel, F. M. et al. (eds.) Greene Publishing Associates, (1989), and other standard laboratory manuals. Other known viral vectors for gene therapy include adenovirus and adeno-associated viruses, including for delivery of DNA to cells of the nervous system as described in U.S. Pat. No. 6,180,613, and baculovirus-derived vector reported by Sarkis C et al., (Efficient transduction of neural cells in vitro and in vivo by a baculovirus-derived vector. Proc Natl Acad Sci USA 2000 Dec 19; 97:14638-43).

Where a large amount of DNA may be required to achieve cell-specific gene expression, non-viral, polymeric gene carriers which can incorporate large DNA plasmids may be used as a carrier in gene therapy. These carriers include cationic polymers or lipids as described in Davis M E, Non-viral gene delivery system; Current opinion in biotechnology 2002, 13: 128-131; Niidome T and Huang L, Hene therapy progress and prospects: nonviral vectors. Gene Therapy, 2002, 9:1647-1652; Li S and Huang L, Nonviral gene therapy: promises and challenges. Gene Therapy, 2000, 7: 31-34; Boussif O, Lezoualc'h F, Zanta M A, Mergny M D, Scherman D, Demeneix B, Behr J-P. A versatile vector for gene and oligonucleotide transfer into cells in culture and in vivo: Polyethylenimine. Proc. Natl. Acad. Sci. USA, 1995; 92: 7297-7302; Abdallah B, Hassan A, Benoist C, Goula D, Behr J P, Demeneix B A. A powerful nonviral vector for in vivo gene transfer into the adult mammalian brain: polyethylenimine. Hum Gene Ther.1996; 7: 1947-1954; Goula D, Remy J S, Erbacher P, Wasowicz M, Levi G, Abdallah B, Demeneix B A. Size, diffusibility and transfection performance of linear PEI/DNA complexes in the mouse central nervous system. Gene Therapy, 1998; 5:712-717.

Plasmid DNA complexed with a cationic polymer such as polyethylenimine (PEI) can be delivered to neuronal cells and in one embodiment, the method of treating a neuronal disorder further comprises the step of mixing the expression vector with a polymeric gene carrier prior to administration. In one embodiment, the polymeric gene carrier is PEI.

To deliver the vector specifically to neuronal cells in a particular region of the central nervous system, it may be administered by stereotaxic microinjection as is known in the art and as described in the examples. For human patients, the stereotactic frame base will be fixed into the skull and the brain with the stereotactic frame base will be imaged using high resolution MRI. Using appropriate stereotactic software, the images will be translated into 3 dimensional coordinates appropriate for the stereotactic frame for targeted injection of vector DNA.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

The word "comprising" is used as an open-ended term, substantially equivalent to the phrase "including, but not limited to". The following examples are illustrative of various aspects of the invention, and do not limit the broad aspects of the invention as disclosed herein.

EXAMPLES

1. Materials and Methods

Plasmid Construction

PGL3-basic vector was purchased from Promega. psub-PDGF-EGFP (Patema et al., 2000) was kindly provided by Prof. H Büeler (Institute of Molecular Biology, University of Zurich, Switzerland). The luciferase constructions of pCMVIE-PDGF-luc, pCMVIEluc, pPDGFluc, pCMVluc were based on pGL3-basic vector. To generate pCMVIE-PDGF-luc, PDGF-β promoter and CMV immediate early (CMVIE) enhancer were amplified from psubPDGF-EGFP and pRc/CMV$_2$ (Invitrogen life technologies, California, USA) using PCR and inserted between Sac I/Hind III and Kpn I/Sac I respectively in the multiple cloning sites of pGL3-basic vector. pCMVIEluc and pPDGFluc were constructed by inserting PCR products of CMVIE enhancer and PDGF promoter into Kpn I/Sac I and Sac I/Hind III sites of pGL3-basic vector. To construct pCMVluc, CMV full-length promoter was amplified from pRc/CMV$_2$ and inserted into Kpn I/Hind III sites of pGL3-basic vector. Schematic structures of the four different plasmid vectors used in this study are shown in FIG. 1.

All plasmid DNAs were amplified in DH5α *E.coli* and purified according to a standard protocol (Qiagen, Hilden, Germany). Plasmid obtained by PCR amplification were verified by DNA sequencing. Oligonucleotides used for PCR amplification are listed as follows with restriction sites shown in italics.

CMVIE enhancer:

sense primer,      5'- ATTC*GGTACC* CCTGGGTCGACATTGA-3'     (SEQ. ID NO. 1)

antisense primer, 5'- CAAC*GAGCTC* ACCATGGTAATAGCGATG-3'  (SEQ. ID NO. 2)

CMV promoter:

sense primer,      5'-ATTA*GGTACC* CGATGTACGGGCCAGATATACG-3'  (SEQ. ID NO. 3)

antisense primer, 5'- TAAT*AAGCTT* ACTAGTGGATCCGAGCTCGGTA-3' (SEQ. ID NO. 4)

PDGF-β promoter:

sense primer,      5'-AATT*GAGCTC*CTAGAGGATCCACAGTCT-3'   (SEQ. ID NO. 5)

antisense primer, 5'-CAGC*AAGCTT*TTCAGTTCCTCGACTCTAG-3' (SEQ. ID NO. 6)

Preparation of DNA/Polymer Complexes

Plasmid DNA was diluted in 5% glucose. PEI (25 kDa; Sigma-Aldrich, San Diego, Calif.) was used as a 10 mM aqueous stock solution. Relative amounts of PEI to DNA for cell transfection and animal experiments were 10 and 14 equivalents of PEI nitrogen per DNA phosphate respectively. The required amount of PEI was calculated by taking into account that 1 µg DNA contains 3 nmol of phosphate and that 1 µl of 10 mM PEI holds 10 nmol of amine nitrogen. Complexes were formed by adding the appropriate amount of PEI solution into the DNA solution, mixing with brief vortex, and waiting for 30 min at room temperature.

Preparation of Viral Vectors

Recombinant baculoviruses were constructed using the Bac-To-Bac Baculovirus Expression System (Gibco BRL, Life Technologies, Gaithersburg, Md., USA). Luciferase cDNA under the CMV promoter or CMVIE enhancer and PDGF-βpromoter were inserted into the transfer plasmid pFastBac1, with the CMV or CMVIE enhancer and PDGF-β promoter inserted between Not1 & Xba1, and luciferase cDNA inserted between Xho1 & HindIII. Recombinant baculoviruses produced were propagated in Sf9 insect cells according to standard methods published by O'Reilly D R, Miller L K, and Luchow V A (Baculovirus Expression Vectors: A Laboratory Manual. New York: W.H. Freeman and Company, 1992). Budded viruses from insect cell culture medium were filtered through a 0.2-um pore size filter and concentrated by ultrafiltration. The viral pellet was resuspended in PBS and infectious titers were determined by plaque assay on Sf9 cells.

Recombinant adeno-associated viruses (AAV) were constructed using the AAV Helper-Free System (Stratagene, La Jolla, Calif.). The CMV, PDGF β and CMVIE enhancer-PDGF β promoter constructs were inserted into pAAV-luciferase between the Kpn I and Hind III, to generate AAV expression plasmids, pAAV-CMV-luc, pAAV-PDGF-luc and pAAV-CMVIE/PDGF-luc, respectively. All plasmids were amplified in *Escherichia coli* DH5α strain and prepared using Qiagen plasmid Maxi-prep Kit (Qiagen, Ontario, Canada). Recombinant, replication-deficient AAV-2 virions are produced through co-transfection of one of the above three AAV expression plasmid, AAV packaging plasmid pAAV-RC and adenovirus helper plasmid pHelper (1:1:1 molar ratio) in HEK293 cells by PEI method. Three days after transfection, the cells were collected and AAV were released from the cells by two rounds of freeze/thaw cycles. AAV particles were purified by a single-step gravity-flow heparin affinity column, as described by Auricchio A et al. (Isolation of highly infectious and pure adeno-associated virus type 2 vectors with a single-step gravity-flow column. Hum Gene Ther. 2001; 12:71-76). The titers of the purified AAV particles were determined by an ELISA kit from Progen, Germany.

Cell Cultures

The in vitro transfection experiment was performed in rat pheochromocytoma PC12 cells, neonatal mouse cerebellum stem cells MTC 17.2 and rat primary cortex neurons. MTC 17.2 and primary neurons were grown in DMEM supplemented at 37° C. with 10% FBS in an atmosphere of 5% $CO_2$ and PC12 cells were grown in RPMI 1640 containing 15% FCS.

Transfection Into Cultured Cells and Luciferase Activity Assay

For the transfection of PC12 and MTC 17.2, the cells were split one day prior to transfection and plated in 24-well plates at a cell density of $5\times10^4$ per well with 0.5 ml of the above indicated medium. After overnight incubation, the culture medium was replaced with 300 µl Opti-MEM and an aliquot of 10 µl of the DNA/PEI complexes containing 0.1 pmole DNA was added to each well of the plates. DNA/PEI complexes were incubated with the cells for 3 hours at 37° C. The medium was replaced with 0.5 ml of fresh complete medium and cells were further incubated for 24 hours. After the incubation, cells were permeabilized with 100 µl of cell lysis buffer (Promega). For the transfection of rat primary cortex neurons, the cells were seeded into 46-well plates for baculovirus infection or 96-well plates for AAV infection. The luciferase activity in cell extracts was measured using a luciferase assay kit (Promega). The relative light units (RLU) were normalized against protein concentration in the cell extracts, which was measured using a protein assay kit (Bio-Rad labs, Hercules, Calif).

In vivo Study

Animals

Adult male Wistar rats (weighing 250-320 g) were used in this study. The rats were divided into several groups: for luciferase extraction study, 4 rats were used for each time interval: pCMVIE-PDGF-luc (n=32), pCMVIEluc (n=4), pPDGFluc (n=4), pCMVluc (n=12); for immunohistochemical study: sham operated group (n=6), pCMVIE-PDGF-luc injected group (n=6), pCMVluc injected group (n=6); for PCR analysis (n=3). Rats were randomly assigned to each group at various times after injection. They were kept 4 to a cage in a light-dark cycle (12 h/12 h) at a constant temperature of 22° C. and at 60% humidity, and fed with normal laboratory rat food. In the handling and care of all animals, the International Guiding Principles for Animal Research as stipulated by World Heath Organization (1985) and as adopted by the Laboratory Animal Center, National University of Singapore, were followed. All rats were bred and supplied by the Laboratory Animal Center, National University of Singapore, and kept in the animal unit before and after the experiments.

Injection Procedures

Rats were anaesthetized by an intraperitoneal injection of sodium pentobarbital (60 mg/kg of body weight) and positioned in a stereotaxic instrument with the nose bar set at 0 (for striatum injection) or −3.5 mm (for hippocampus injection). DNA was separately bilaterally injected into the striatum at 3 injection points [coordinates (from bregma and dura): anterior (A), +1.5 mm, lateral (L), +2.0 mm, ventral (V), −5.0 mm; A, +0.5 mm, L, +3 mm, V, −5.0 mm and A, −0.3 mm, L, +3 mm, V, −5.0 mm] or into the hippocampus (coordinates: A, −4.4 mm, L, +3.2 mm, V,−2.5 mm). For each injection, the injection value was 5 µl which contained 1 µg DNA in PEI/DNA complex. The rate of injection was 1 µl/minute and the needle was allowed to remain in situ for 5 minutes before being slowly retracted at the end of each injection.

PCR Detection of Luciferase Gene from Tissue Samples

Tissue samples of striatum, hippocampus, cortex and substantia nigra were collected from rat brains 2 days after striatum injection of pCMVIE-PDGF-Luc. The tissues were homogenized by mincing with a razor blade and plasmid DNA was extracted according to the standard protocol of a DNeasy Tissue Kit (Qiagen). The oligonucleotide primers for luciferase PCR are listed below:

```
5' primer:  5'-AT TGC TCA ACA GTA TGG GCA-3'    (SEQ. ID NO. 7)

3' primer:  5'-CGA AGA AGG AGA ATA GGG TTG-3'   (SEQ. ID NO. 8)
```

The expected size of the amplified product is 540 bp. Amplification cycles consisted of 94° C. 5 min, 1 cycle; 94° C., 45 s, 55° C. 30 s, 72° C., 30 s, 35 cycles with a final extension at 72° C. for 7 min. To exclude contamination of the whole process, a normal rat brain with the injection of PEI was handled in parallel.

Luciferase Assay

Following deep anesthesia, rats were sacrificed by intracardiac perfusion with 0.1 M phosphate buffered saline PBS (pH 7.4). The brains were removed and the four different parts including striatum, hippocampus, cortex and substantia nigra were dissected and separately collected into eppendorf tubes. Tissue samples were stored at −80° C. until processing. After adding PBS buffer separately (100 µl PBS per 50 mg tissue), each sample was homogenized by sonication for 10 seconds on ice, and then centrifuged at 13,000 rpm at 4° C. in a microcentrifuge. Ten microliters of the supernatant at room temperature was used for the luciferase activity assay employing an assay kit from Promega. Measurements were made in a single-well luminometer (Berthold Lumat LB 9501) for 10 seconds.

Immunohistochemical Analyses

Two days after injection with pCMVIE-PDGF-luc, pCMVluc or sham operation, rats were sacrificed (n=3). Following deep anesthesia, all rats were perfused first with Ringer's solution followed by 2% paraformaldehyde in 0.1 M PBS (pH 7.4). After perfusion, the cerebral cortices containing the striatum and hippocampus were removed and post-fixed in the same fixative for 2-4 hours before they were transferred into 0.1 M PBS containing 15% sucrose and kept overnight at 4° C. Frozen coronal sections of each brain were cut at 30 µm thickness and collected before being stored in 0.1 M PBS.

Free-floating sections were washed for 20 min in 0.1M PBS at pH 7.4 containing 0.2% Triton X-100, then blocked with 5% normal goat serum in PBS for 1 hour. Sections were then incubated overnight with primary antibodies polyclonal anti-luciferase (Promega; dilution 1:150) and monoclonal against neuron-specific nuclear protein (NeuN) (Chemicon International, USA; dilution 1:500). Sections were washed in 0.1 M PBS and further incubated with anti-rabbit IgG Tritc conjugate (Sigma-Aldrich, Inc., USA; dilution 1:100) and anti-mouse IgG Fitc conjugate (Sigma-Aldrich; dilution 1:100) for 1 hour. After incubation, sections were washed three times in PBS. They were then collected on gelatin-coated slides, mounted with DAKO fluorescent mounting medium and covered with coverslips. Control sections were incubated without primary antibodies.

Visualization of Double Labeling with Confocal Scanning Microscopy

Sections were examined with a Carl Zeiss LSM410 confocal laser scanning microscope. Each section was initially scanned with a 488 nm laser line, and an emission filter BP 510-525, for the detection of Fitc fluorescein; and with a 543 nm laser line, and an emission filter LP 570, for the detection of Tritc fluorescein.

Quantitative Analysis

Three rats each were used in cell quantification for colocalization of pCMVIE-PDGF-luc and pCMV-luc with NeuN. Four sections for each rat were selected randomly and used for cell counting. A total of 3 bilateral fields selected randomly were surveyed in each section. Each field was captured under a Carl Zeiss LSM410 confocal laser scanning microscope at magnification of 200×. Colocalized cells in each picture were counted and percentages of colocalization of NeuN in pCMVIE-PDGF-luc and pCMV-luc positive cells were calculated respectively. Student's t-test was used to determine the statistical significance of extent of colocalization in different plasmids.

2. Results

Table 1. The numbers of luciferase immunoreactivity positive cells that contain or lack the neuron-marker NeuN immunoreactivity from rats sacrificed at 2 days post-injection of pCMVIE-PDGF-luc or pCMVluc into either the striatum or the hippocampus.

| Injection Sites | Striatum | Hippocampus |
|---|---|---|
| Number of Luciferase and positive cells per field (Mean ± S.E.M.): | | |
| CMVIE-PDGF | 61.17 ± 7.17 | 31.94 ± 1.58 |
| CMV | 106.17 ± 5.89 | 82.78 ± 4.67 |
| Number of Luciferase and NeuN double labeled cells per field (Mean ± S.E.M.): | | |
| CMVIE-PDGF | 55.89 ± 8.37 | 28.5 ± 2.03 |
| CMV | 51.00 ± 2.19 | 41.78 ± 2.34 |
| Percentage of transfected neurons* (Mean ± S.E.M.): | | |
| CMVIE-PDGF | 91.28% ± 4.06% | 89.29% ± 2.83% |
| CMV | 48.08% ± 1.08% | 50.54% ± 3.46% |

*Percentage of transfected neurons = the number of double labeled cells/total number of luciferase immunoreactive cells.

Increased In vitro Gene Expression by Using the Chimeric Promoter of CMVIE-PDGF

To eliminate the effect of different plasmid backbone on gene expression, all luciferase reporter plasmids were constructed under the same backbone of pGL3-basic vector (FIG. 1). Luciferase expression from pCMVIE-PDGF-Luc was compared in vitro with those from pCMVluc, pPDG-Fluc and pCMVIEluc following the transfection of neuronal cells. As shown in FIG. 2, pCMVIE-PDGF-Luc drove dramatically increased expression when compared with pPDGFluc and pCMVIEluc in the two tested cells. In these cells, the activity of PDGF in pCMVIE-PDGF-Luc increased 8 fold in PC12 and 90 fold in MTC17.2 as compared with that from pPDGFluc. The enhancement was far superior to the expression from the simple sum up of PDGF and CMVIE by themselves. Ratios between the levels of expression from pCMVIE-PDGF-Luc and pCMVluc in PC12 and MT C17.2 cells were 0.88 and 2.92 respectively, indicating that the chimeric promoter increased gene expression to nearly or even higher than that of the CMV promoter in these two neuronal-cell lines.

Neuron-specificity of the Chimeric Promoter CMVIE-PDGF in the Brain

We then investigated if the CMVIE-PDGF promoter could maintain neuronal specificity of PDGF-β promoter. Sections from rats that received either striatal or hippocampal injections of pCMVIE-PDGF-luc and pCMVluc were co-stained with antibodies against both luciferase and a neuronal marker, NeuN. In the hippocampus, the patterns of expression of CMVIE-PDGF-luc and CMV were very different. The CMVIE-PDGF-luc expressing cells were mostly in the granular neuronal cell layer. Immunohistochemical colocalization of the CMVIE-PDGF-luc stained cells with the NeuN marker showed that most of these cells were neuronal (FIG. 3). Cell counts demonstrated that 89% of the cells in hippocampus that contained luciferase also contained NeuN (Table 1). In contrast, the CMV-luc expressing cells had a diffuse anatomical distribution spread out from the neuronal cell layers, corresponding to neurons, astrocytes and glial cells. Quantative analysis showed that only 50% of the luciferase stained cells are neurons (Table 1). In the striatum, the CMV-luc stained cells had a diffused distribution, whereas the CMVIE-PDGF-luc were restricted to neurons (FIG. 4), same as observed in the hippocampus. Cell counts demonstrated that the proportion of luc expressing neurons for CMVIE-PDGF-Luc was 91%, significantly higher than that for CMV-Luc (48%) (Table 1).

Increased In vivo Gene Expression by Using the Chimeric Promoter of CMVIE-PDGF

The efficiencies of CMVIE-PDGF, PDGF-β and CMVIE enhancer promoters in inducing luciferase expression in vivo were compared following injection into the rat striatum. Tissue samples were collected from the striatum of each rat brain for luciferase assays. Levels of luciferase activity expressed by each plasmid are presented in FIG. 5. Luc expression was detected in all of the four plasmid constructs as early as 24 hour post-injection. Expression from CMVIE-PDGF-luc increased up to 5 days then remained stable until day 14. The expression levels of CMVIE and PDGF-β were low 1 day post-injection and became undetectable after 3 days (data not shown), suggesting the weak activities of these two promoters. Similar to that observed in in vitro study, the activity of CMVIE-PDGF was enhanced in vivo when compared with CMVIE and PDGF-β promoter.

Increased Gene Expression by Using the Chimeric Promoter of CMVIE-PDGF in the Context of Viral Vectors Plasmid DNA vectors were used in the above studies. To test whether the chimeric promoter of CMVIE enhancer-PDGF β promoter may also increase gene expression after insertion into a viral vector, we generated recombinant baculoviruses and adeno-associated viruses containing the chimeric promoter and tested them in cell cultures of rat primary cortex neurons and in rat brain. As shown in FIG. 6A, the CMVIE enhancer—PDGF β promoter significantly increased gene expression, as compared with PDGF β promoter, by 19-fold when AAV vectors were used and 15-fold when baculovirus vectors were used. The enhancement was far superior to the expression from the simple sum up of PDGF β promoter and CMVIE enhancer by themselves, as well as to the expression from the CMV promoter. Following injection into the rat striatum, the CMVIE enhancer—PDGF β promoter in the AAV vectors drove higher levels of in vivo gene expression than the PDGF β and CMV promoters, displaying a 5-fold increase (FIG. 6B).

What is claimed is:

1. A recombinant nucleic acid molecule comprising a neuronal cell specific PDGF β promoter consisting of SEQ ID NO. 10 operably coupled downstream to a CMVIE enhancer consisting of SEQ ID NO. 9 wherein the CMVIE enhancer increases the neuronal cell specific transcriptional activity of the PDGF β promoter.

2. The nucleic acid molecule according to claim 1 comprising the sequence of SEQ ID NO. 11.

3. The nucleic acid molecule according to claim 2 further comprising a coding sequence operably linked to the promoter.

4. The nucleic acid molecule according to claim 3 wherein the coding sequence is a therapeutic gene sequence.

5. An expression vector comprising a nucleic acid molecule according to claim 3.

6. The vector according to claim 5 wherein the vector is a plasmid.

7. The vector according to claim 5 wherein the vector is a virus or virus derived.

8. The vector according to claim 7 wherein the vector is a baculovirus or adeno-associated virus.

9. A method of expressing a gene in a neuronal cell comprising transforming a neuronal cell with the expression vector according to claim 5.

10. An isolated transgenic cell comprising a recombinant nucleic acid molecule comprising a neuronal cell specific PDGFβ promoter consisting of SEQ ID NO: 10 operably coupled downstream to the CMVIE enhancer consisting of SEQ ID NO: 9, wherein the CMVIE enhancer increases the neuronal specific transcriptional activity of the PDGFβpromoter.

11. A method of increasing the neuronal cell-specific transcriptional activity of the PDGF β promoter consisting of SEQ ID NO. 10 comprising operably linking a heterologous CMVIE enhancer consisting of SEQ ID NO. 9 upstream to the PDGF β promoter.

12. An expression vector comprising a nucleic acid molecule according to claim 4.

13. The vector according to claim 12 wherein the vector is a plasmid.

14. The vector according to claim 12 wherein the vector is a virus or virus derived.

15. The vector according to claim 14 wherein the vector is a baculovirus or adeno-associated virus.

16. The isolated transgenic cell according to claim 10 comprising the sequence of SEQ ID NO: 11.

17. The isolated transgenic cell according to claim 16 further comprising a coding sequence operably linked to the promoter.

18. The isolated transgenic cell according to claim 17 wherein the coding sequence is a therapeutic coding sequence.

19. The method of claim 9 wherein the expression vector is a plasmid.

20. The method of claim 9 wherein the expression vector is a virus or virus derived.

21. The method of claim 9 wherein the vector is a baculovirus or adeno-associated virus.

22. The method of claim 9 wherein the coding sequence is a therapeutic gene

23. The method of claim 22 wherein the expression vector is a plasmid.

24. The method of claim 22 wherein the expression vector is a virus or virus derived.

25. The method of claim 22 wherein the expression vector is a baculovirus or adeno-associated virus.

* * * * *

UNITED STATES PATENT AND TRADEMARK OFFICE
CERTIFICATE OF CORRECTION

PATENT NO. : 7,341,847 B2
APPLICATION NO. : 10/407009
DATED : March 11, 2008
INVENTOR(S) : Shu Wang, Beihui Liu and Xu Wang It is certified that error appears in the above-identified patent and that said Letters Patent is hereby corrected as shown below:

In Claim 18 (Col. 30, line 49), "therapeutic coding sequence" should be

--therapeutic gene sequence--.

Signed and Sealed this

Seventeenth Day of March, 2009

JOHN DOLL
*Acting Director of the United States Patent and Trademark Office*

```
                           SEQUENCE LISTING

<160> NUMBER OF SEQ ID NOS: 11

<210> SEQ ID NO 1
<211> LENGTH: 26
<212> TYPE: DNA
<213> ORGANISM: Artificial
<220> FEATURE:
<223> OTHER INFORMATION: Primer

<400> SEQUENCE: 1
attcggtacc cctgggtcga cattga                                          26

<210> SEQ ID NO 2
<211> LENGTH: 28
<212> TYPE: DNA
<213> ORGANISM: Artificial
<220> FEATURE:
<223> OTHER INFORMATION: Primer

<400> SEQUENCE: 2
caacgagctc accatggtaa tagcgatg                                        28

<210> SEQ ID NO 3
<211> LENGTH: 32
<212> TYPE: DNA
<213> ORGANISM: Artificial
<220> FEATURE:
<223> OTHER INFORMATION: Primer

<400> SEQUENCE: 3
attaggtacc cgatgtacgg gccagatata cg                                   32

<210> SEQ ID NO 4
<211> LENGTH: 32
<212> TYPE: DNA
<213> ORGANISM: Artificial
<220> FEATURE:
<223> OTHER INFORMATION: Primer

<400> SEQUENCE: 4
taataagctt actagtggat ccgagctcgg ta                                   32

<210> SEQ ID NO 5
<211> LENGTH: 28
<212> TYPE: DNA
<213> ORGANISM: Artificial
<220> FEATURE:
<223> OTHER INFORMATION: Primer

<400> SEQUENCE: 5
aattgagctc ctagaggatc cacagtct                                        28

<210> SEQ ID NO 6
<211> LENGTH: 29
<212> TYPE: DNA
<213> ORGANISM: Artificial
```

```
<220> FEATURE:
<223> OTHER INFORMATION: Primer

<400> SEQUENCE: 6
cagcaagctt ttcagttcct cgactctag                                              29

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
attgctcaac agtatgggca                                                        20

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
cgaagaagga gaatagggtt g                                                      21

<210> SEQ ID NO 9
<211> LENGTH: 387
<212> TYPE: DNA
<213> ORGANISM: Cytomegalovirus
<220> FEATURE:
<221> NAME/KEY: misc_feature
<223> OTHER INFORMATION: cytomegalovirus immediate early enhancer

<400> SEQUENCE: 9
cctgggtcga cattgattat tgactagtta ttaatagtaa tcaatacggg gtcattagtt            60
catagcccat atatggagtt ccgcgttaca taacttacgg taaatggccc gcctggctga          120
ccgcccaacg accccgccc attgacgtca ataatgacgt atgttcccat agtaacgcca          180
atagggactt tccattgacg tcaatgggtg gactatttac ggtaaactgc ccacttggca          240
gtacatcaag tgtatcatat gccaagtacg ccccctattg acgtcaatga cggtaaatgg          300
cccccctggca ttatgcccag tacatgacct tatgggactt tctacttggc agtacatcta          360
cgtattagtc atcgctatta ccatggt                                              387

<210> SEQ ID NO 10
<211> LENGTH: 1488
<212> TYPE: DNA
<213> ORGANISM: human
<220> FEATURE:
<221> NAME/KEY: misc_feature
<223> OTHER INFORMATION: human platelet-derived growth factor
      Beta-chain promoter

<400> SEQUENCE: 10
ctagaggatc cacagtctcc tgagtagctg ggactacagg agcttgttac cacacccagc            60
tccagtttat aaattcatct ccagtttata aaggaggaaa ccgaggtact gagaggttaa          120
aaaaccttcc tgcagacact tgtccagcaa gtggccactc caggatttgg accaaggtga          180
tgtgtcttca ggctgtgtct ctgccactgt gccacgctgc tgggtggtag gcagcagtgg          240
gtgggtgcct gcagtggtct gtaaagacca cctgagatgt ccttcctcct ctgttccacc          300
ctgtccaggt ccaagaagac agtctatgaa gagagagcag gtgtgactct ctcagtgtgc          360
```

```
tcctctgtga agcaggct gacatcccaa agggaagggc ggataacaga gacagtgcaa      420
gcggaggaga tgagggtgcc tcaaagccgg gaggctgggt gatgcaggag cctgcgtgtc    480 ccgaggggg tgctgggccc agtgtgagta cgtgtgactg tgactgagac agtgtgactg    540
ctgaaggcag ggacacagca gctccctgac tgggggcaga aggcgttaac tgtgtgaagg    600
ctggttgtgg gtgggtgggc tctgggcctc gaacccgggg gctgagggag atagtaaaca    660
gcagggtgac tgacgggaag atcatgttgg tagccctgcg aagatgctgc agggctgtgg    720
gggtttgtgt gactttgcag ttcaacaaat tcaaattcag ccaacgctgg cagggcctgt    780
tgtgccaggc aaccagctag gaggaggaga ctcggaccca gcttgcagct gaagggcgct    840
ggctgccggg ttctgtgggt tcaccttgcg gtgtcttccc ttgctaacac tgagtcctta    900
caatagcccc atctccaggt tgaggctaga tggagggac agagggaagt gacttgccca    960
aggtgaccca agctcccgag tgccaggca ggatctgaat tcaggctctc agactgcaga  1020
gcctgagtcc ctccctgcca tgcctgtgcc agggtggaaa tgtctggtcc tggaggggag  1080
cgtggactcc tggccttggc tctggagaca tcccctaga ccacgtgggc tcctaacctg   1140
tccatggtca ctgtgctgag gggcgggacg gtgggtcacc cctagttctt ttttccccag   1200
ggccagattc atggactgaa gggttgctcg gctctcagag acccctaag cgccccgccc    1260 tggccccaag ccctccccca gctcccgcgt ccccccctc ctggcgctga ctccgggcca    1320
gaagaggaaa ggctgtctcc acccacctct cgcactctcc cttctccttt ataaaggccg   1380
gaacagctga aagggtggca acttctcctc ctgcagccgg gagcggcctg cctgcctccc   1440
tgcgcacccg cagcctcccc cgctgcctcc ctagagtcga ggaactaa                1488
```

```
<210> SEQ ID NO 11
<211> LENGTH: 1881
<212> TYPE: DNA
<213> ORGANISM: Artificial
<220> FEATURE:
<223> OTHER INFORMATION: CMVIE-PDGF-Beta chimeric promoter

<400> SEQUENCE: 11
cctgggtcga cattgattat tgactagtta ttaatagtaa tcaatacggg gtcattagtt     60
catagcccat atatggagtt ccgcgttaca taacttacgg taaatggccc gcctggctga   120
ccgcccaacg accccccgccc attgacgtca ataatgacgt atgttcccat agtaacgcca   180
atagggactt tccattgacg tcaatgggtg gactatttac ggtaaactgc ccacttggca   240
gtacatcaag tgtatcatat gccaagtacg ccccctattg acgtcaatga cggtaaatgg   300 cccgcctggca ttatgcccag tacatgacct tatgggactt tcctacttggc agtacatcta   360 cgtattagtc atcgctatta ccatggtgag ctcctagagg atccacagtc tcctgagtag   420
ctgggactac aggagcttgt taccacaccc agctccagtt tataaattca tctccagttt    480
ataaaggagg aaaccgaggt actgagaggt taaaaacct tcctgcagac acttgtccag    540
caagtggcca ctccaggatt tggaccaagg tgatgtgtct tcaggctgtg tctctgccac    600
tgtgccacgc tgctgggtgg taggcagcag tgggtgggtg cctgcagtgg tctgtaaaga    660
ccacctgaga tgtccttcct cctctgttcc accctgtcca ggtccaagaa gacagtctat    720
gaagagagag caggtgtgac tctctcagtg tgctcctctg tgaagcagg ctgacatcc     780 caaagggaag ggcggataac agagacagtg caagcggagg agatgagggt gcctcaaagc    840
cgggaggctg ggtgatgcag gagcctgcgt gtccgaggg gggtgctggg cccagtgtga     900
```

```
gtacgtgtga ctgtgactga gacagtgtga ctgctgaagg cagggacaca gcagctccct        960
gactgggggc agaaggcgtt aactgtgtga aggctggttg tgggtgggtg ggctctgggc       1020
ctcgaacccg ggggctgagg gagatagtaa acagcagggt gactgacggg aagatcatgt       1080
tggtagccct gcgaagatgc tgcagggctg tgggggtttg tgtgactttg cagttcaaca       1140
aattcaaatt cagccaacgc tggcagggcc tgttgtgcca ggcaaccagc taggaggagg       1200
agactcggac ccagcttgca gctgaagggc gctggctgcc gggttctgtg ggttcacctt       1260
gcggtgtctt cccttgctaa cactgagtcc ttacaatagc cccatctcca ggttgaggct       1320
agatggaggg gacagaggga agtgacttgc ccaaggtgac ccaagctccc gagtgccagg       1380
gcaggatctg aattcaggct ctcagactgc agagcctgag tccctccctg ccatgcctgt       1440
gccagggtgg aaatgtctgg tcctggaggg gagcgtggac tcctggcctt ggctctggag       1500
acatccccct agaccacgtg ggctcctaac ctgtccatgg tcactgtgct gaggggcggg       1560
acggtgggtc acccctagtt cttttttccc cagggccaga ttcatggact gaagggttgc       1620
tcggctctca gagaccccct aagcgcccg ccctggcccc aagccctccc ccagctcccg       1680
cgtccccccc ctcctggcgc tgactccggg ccagaagagg aaaggctgtc tccacccacc       1740
tctcgcactc tcccttctcc tttataaagg ccggaacagc tgaaagggtg gcaacttctc       1800
ctcctgcagc cgggagcggc ctgcctgcct ccctgcgcac ccgcagcctc ccccgctgcc       1860
tccctagagt cgaggaacta a                                                 1881
```